US007553662B2

(12) United States Patent
El Haj et al.

(10) Patent No.: US 7,553,662 B2
(45) Date of Patent: Jun. 30, 2009

(54) CULTURING TISSUE USING MAGNETICALLY GENERATED MECHANICAL STRESSES

(75) Inventors: Alicia Jennifer Hafeeza El Haj, High Peak (GB); Jon Paul Dobson, Stoke-on-Trent (GB)

(73) Assignee: Keele University, Keele Staffordshire (GB)

( * ) Notice: Subject to any disclaimer, the term of this patent is extended or adjusted under 35 U.S.C. 154(b) by 496 days.

(21) Appl. No.: 10/451,249

(22) PCT Filed: Dec. 19, 2001

(86) PCT No.: PCT/GB01/05606

§ 371 (c)(1),
(2), (4) Date: Mar. 25, 2004

(87) PCT Pub. No.: WO02/051985

PCT Pub. Date: Jul. 4, 2002

(65) Prior Publication Data

US 2004/0147015 A1    Jul. 29, 2004

(30) Foreign Application Priority Data

Dec. 22, 2000  (GB) ................................ 0031462.5
Dec. 23, 2000  (GB) ................................ 0031651.3

(51) Int. Cl.
 *C12N 5/00* (2006.01)
(52) U.S. Cl. ..................... 435/373; 435/325; 977/773; 977/828
(58) Field of Classification Search ................. 435/325, 435/373
See application file for complete search history.

(56) References Cited

U.S. PATENT DOCUMENTS

| 4,105,017 | A | * | 8/1978 | Ryaby et al. .................... 600/14 |
| 5,183,336 | A | * | 2/1993 | Poltorak et al. ............. 366/273 |
| 5,486,457 | A | * | 1/1996 | Butler et al. .................. 435/7.2 |
| 5,842,477 | A | * | 12/1998 | Naughton et al. ........... 128/898 |
| 6,197,586 | B1 | * | 3/2001 | Bhatnagar et al. ........... 435/395 |
| 6,548,264 | B1 | | 4/2003 | Tan et al. .................... 435/7.21 |
| 6,649,408 | B2 | * | 11/2003 | Bailey et al. ................. 435/325 |
| 2006/0093611 | A1 | | 5/2006 | El Haj et al. |

FOREIGN PATENT DOCUMENTS

WO    05059118 A2    6/2005

OTHER PUBLICATIONS

XP-001061490, "Differentiation of Myoblasts is Accelerated in Culture in a Magnetic Field", Louis Yuge and Katsuko Kataoka; Inst. of Health Sciences (L.Y.) and Dept. of Anatomy (K.K.), Faculty of Medicine, Hiroshima; Jun. 2000 Society for In Vitro Biology; pp. 383-386.
XP-001080069, "Bio-Stretch, A Computerized Cell Strain Apparatus for Three-Dimensional Organotypic Cultures", Mingyao Liu et al., Feb. 1999 Society for In Vitro Biology, pp. 87-93.
XP-002203098, "Dynamic cell stretching increases human osteoblast proliferation and CICP synthesis but decreases osteocalcin synthesis and alkaline phosphatase activity", D. Kaspar, et al., Journal of Biomechanics 33 (2000), pp. 45-51.
XP-001080015, "A Cell Strain System for Small Homogeneous Strain Applications", M. Bottlang et al., Biomed. Technik 42 (1997), pp. 305-309.
XP-002203099, "A new method for application of force to cells via ferric oxide beads", Michael Glogauer et al., Eur. J. Physiol. (1998) 435: 320-327.
XP-002203103, "Magnetic fields applied to collagen-coated ferric oxide beads induce stretch-activated Ca-2+ flux in fibroblasts", M. Glogauer et al., American Journal of Physiology, 1995 269: C1093-C1104 abstract only.
XP-002203100, "Induction of NO and prostaglandin $E_2$ in osteoblasts by wall-shear stress but not mechanical strain", R. Smalt et al., 1997 American Physiological Society, 0193-1849/97, pp. E751-E758.
XP-002203101, "Contribution of intermediate filaments to cell stiffness, stiffening, and growth", Ning Wang et al., Am J Physiol Cell Physiol 279: C188-C194, 2000.
XP-002203102, "Mechanical Interactions Among Cytoskeletal Filaments", Ning Wang, 1998 American Hearth Association, Inc., pp. 162-165.
"Compliance of the Hair Bundle Associated with Gating of Mechanoelectrical Transduction Channels in the Bullfrog's Saccular Hair Cell", J. Howard et al., Neuron, vol. 1, 189-199, May 1988.
Comment on "Constraints on biological effects of weak extremely-low-frequency electromagnetic fields", Joseph L. Kirschvink, Physical Review A, vol. 46, No. 4, Aug. 15, 1992, pp. 2178-2184.
"Structural and magnetic properties of nanoscale iron oxide particles synthesized in the presence of dextran of polyvinyl alcohol", Heath Pardoe et al., Journal of Magnetism and Magnetic Materials 225 (2001) 41-46.
"Application of the Ferromagnetic Transduction Model to D.C. and Pulsed Magnetic Fields: Effects on Epileptogenic Tissue and Implications for Cellular Phone Safety", Jon Dobson et al., Biochemical and Biophysical Research Communications, 227, 718-723 (1996) Art. No. 1575.
"Mechanotransduction pathways in bone: calcium fluxes and the role of voltage-operated calcium channels", A. J. Haj et al., Medical and Biological Engineering & Computing, 1999, vol. 37, pp. 403-409.
"Calcium-Channel Activation and Matrix Protein Upregulation in Bone Cells in Response to Mechanical Strain", L. M. Walker et al., Journal of Cellular Biochemistry, 79:648-661 (2000).
Wang, et al., "Control of Cytoskeletal Mechanics by Extracellular Matrix, Cell Shape, and Mechanical Tension." Biophysical Journal, vol. 66, pp. 2181-2189 (Jun. 1994).
Schmidt, et al., "Mechanical Stressing of Integrin Receptors Induces Enhanced Tyrosine Phosphorylation of Cytoskeletally Anchored Proteins." The Journal of Biological Chemistry, vol. 273, No. 9, pp. 5081-5085 (1998).

* cited by examiner

*Primary Examiner*—Ruth A Davis
(74) *Attorney, Agent, or Firm*—Janet Sleath; Speckman Law Group PLLC

(57) ABSTRACT

A method of culturing tissue comprises growing tissue forming cells whilst subjecting the tissue forming cells to mechanical stresses which are generated magnetically.

22 Claims, 3 Drawing Sheets

CULTURING TISSUE USING MAGNETICALLY GENERATED MECHANICAL STRESSES

The present invention relates to a method of culturing cells and relates more particularly (but not exclusively) to the culturing of cells to form replacement human or animal tissue. The invention relates even more particularly, but again not exclusively, to the culturing of mechano-responsive tissue.

The in vitro cultivation of replacement tissue for humans and animals is an important development allowing the tissue to be grown from cells taken from the patient so that the replacement tissue does not cause rejection problems. Examples of replacement tissues that may be produced for such replacement therapies include connective tissue, bone, cartilage, tendon and pancreas.

The replacement tissue must not only be comprised of the same type of cells as the tissue it is intended to replace but must also have the required, possibly complex, 3-dimensional shape. As such, the replacement tissue is generally grown on or within a suitably shaped scaffold immersed in a culture medium in a bioreactor. The scaffold is a cell growth substrate which is shaped to provide growth of the tissue into the required 3-dimensional form. Within the bioreactor there is a (generally constant) flow of culture medium ensuring that the tissue-forming cells on or within the scaffold continuously receive a supply of nutrients and that the metabolic waste products of the cells are removed. The typically increased volumes of culture medium that can be used in bioreactors, compared to static culture flasks, allow immersion of scaffolds of a range of sizes suitable for production of a number of different tissue types. The perfusion of culture medium throughout the scaffold allows all cells to benefit from viable conditions for growth throughout the structure [1].

In addition, and particularly in the case of mechano-responsive tissue, it may be necessary to subject the tissue forming cells to mechanical stresses during their culture to produce fully functional tissue. Thus, for example, some types of connective tissue such as bone, cartilage, ligament and tendons need to be subjected to mechanical stress during culturing thereof to give the required mechanical properties [2].

The degree of stress needed varies according to the cell types used and tissue types required. A number of ways of producing such stresses are known in the art, including direct mechanical stimulation of the cells, and hydrodynamic compression systems. The former method uses rollers or the like to compress the cells, whereas the latter utilises pulses of increased pressure in the culture medium supplying the bioreactor to mechanically stimulate the cells. None of the known methods of mechanically stimulating cells in order to produce functional tissue are, however, entirely satisfactory for many types of tissue such as bone, tendon and ligaments. Direct mechanical methods are cumbersome, and produce difficulties in maintaining the aseptic conditions required for culture. Hydrodynamic compression methods are generally ineffective. Moreover, all previously known methods suffer from the disadvantages that only one magnitude of stress can be applied across the range of cultured cells at any one time (generally a much higher stress than is required at a cellular level), and that the scaffold upon which the cells are grown must itself have considerable mechanical resilience to withstand the stresses applied to it.

It is therefore an object of the present invention to obviate or mitigate the above mentioned disadvantages.

According to a first aspect of the present invention there is provided a method of culturing tissue comprising growing tissue forming cells while subjecting the cells to mechanical stresses characterised in that the mechanical stresses are generated magnetically.

Thus in accordance with the invention, magnetically generated stresses are applied to the tissue forming cells so as to ensure that fully functional tissue is produced.

The method of the invention may be applied in vitro for the growth of tissue to be implanted in a patient. If effected in vitro it is preferred that the tissue forming cells are cultured on or in a 3-dimensional scaffold and preferably also in a bioreactor through which flows a tissue culture medium. Other types of tissue culture vessels may however be used. It is also possible for the method of the invention to be applied in vivo to grow new tissue in situ within the body of the a patient.

The stresses may be generated by a magnetic material capable of generating a force in response to a magnetic field applied within the bioreactor and transmitting that force to the tissue forming cells being cultured so as to apply the required stresses thereto. In preferred embodiments of the invention, the magnetic material is attached to the tissue forming cells and, for preference, takes the form of micro- or nano-particles, preferably coated magnetic micro- or nano-particles. Alternatively the magnetic material may be a ferrofluid which is inserted into the culture medium. A further possibility is the combined use of magnetic material attached to the cells and a ferrofluid.

Irrespective of the particular magnetic material used, the use of a time-varying magnetic gradient or homogeneous field modulates the movement of the magnetic material and consequently allows stresses to be repeatedly applied to the tissue forming cells. Such stresses may be accurately varied both in their magnitude and direction of application so that the tissue forming cells may be subjected to the required stress forming regime to ensure that fully functional tissue is produced. This can be accomplished by varying the magnetic properties of particles attached to different cells in different regions of the same scaffold (or different scaffolds) or through the use of the spatial variation of field strength in the gradient field.

The magnetic field may be varied at a frequency of, for example, 0.1 to 10 Hz. But, frequencies outside this range can also be used. The magnetic field will typically have a flux density on the order of (but not limited to) 10 mT to 1400 mT.

The magnitude of the stresses applied to the cells will be generally on the order of (but not limited to) 0.1 to 100 piconewtons (pN) and the direction in which the stress is applied may result from a linear, translational motion (due to the gradient, particle does not need to be magnetically blocked) or rotational motion (due to the angle of the particle's magnetization vector with the applied field, must be a magnetically blocked particle) of the magnetic material in the applied magnetic field.

Significant advantages of the present invention are that (as indicated) it is easy to control the direction and magnitude of the applied stresses whilst maintaining aseptic conditions in vitro e.g. in a bioreactor or in vivo since variation of the magnetic field may be controlled remotely. Moreover the stresses that are generated at the cellular level are generally small (e.g. a few piconewtons) [3] and as such any scaffolds (on or in which the tissue forming cells are grown) do not need enhanced mechanical properties.

The method of the invention can be used to produce a variety of tissue types in both bioreactors and in vivo which require mechanical loading or activation of mechanosensitive ion channels. These include (but are not limited to) connective tissue such as bone, cartilage, ligament and tendons. Biopsies of the cells to be cultured may be obtained by standardized procedure [4].

It is also possible for the method of the invention to be applied to tissue constructs comprised of tissues of at least two different types, e.g. bone and cartilage. It is also possible to use human mesenchymal stem cells as a source which are differentiated into chondrocytes or bone cells in situ on or within scaffolds.

As mentioned above, a preferred embodiment of the invention involves attachment of magnetic micro- or nano- particles to the tissue forming cells for the purposes of applying the required stresses thereto. The magnetic micro- and nano-particles may be functionalised and attached to the tissue forming cells prior to seeding of the latter onto a scaffold on or in which the tissue is to be grown. Thus, for example, the micro- and nano-particles may be coated with adhesion molecules, e.g. fibronectin and RGD molecules for attachment to the cells.

The micro- and nano-particles (intended to be attached to the cells) will generally be spherical or elliptical and have a diameter in the range 10 nm to 10 μm.

The particles for attachment to the cells may be coated or uncoated and single or multi-domain. Examples of suitable particles include, but are not limited to:

(i) Coated magnetic microspheres (d=4 μm) available from Spherotech, Inc. These microspheres consist of a magnetically blocked core—coated by a polymer.

(ii) Single-domain, ferrite-doped silica nanoparticles with tunable size (d=50-300 nm) and narrow size distribution [5].

It is not however essential for the magnetic material to be particulate nor that it be attached to the cells. It is possible, for example, for the profusion medium in a bioreactor or in vivo to contain a ferrofluid which is used to generate forces, from an applied magnetic gradient field, to the cells being cultured. The ferrofluid may for example be a PVA/magnetite nanoparticle-based ferrofluid (d=4-10 nm) [6]. It is possible also to use particles attached to the cells in combination with a ferrofluid.

The bioreactor may for example be a modification of an existing bioreactor such as profusion, spinner flask, hydrodynamic compression and rotating vessel systems.

Conveniently the magnetic field is generated outside the tissue culture vessel (if the method is applied in vitro), or outside the body for the case of in vivo applications, and may be provided by a permanent magnet or an electromagnet. In order to generate variable fields, a permanent magnet may be moved relative to the cells being cultured. Thus, in the case of a bioreactor, such movement may for example be longitudinally along the reactor, towards-and-away form the reactor or around the reactor. Any combination of these movements may also be used. In the case of an electromagnet, varying magnetic fields may be generated by provision of appropriate electric current levels to the electromagnet optionally in combination with movement of the electromagnet in the same manner as described for the permanent magnet.

Examples of commercially available magnets that may be used include Neodymium-Iron-Boron and Samarium-Cobalt permanent magnets that are capable of generating the required field gradients and flux densities. They can be geometrically tailored and magnetized to a variety of required specifications and produce flux densities at the surface in excess of 1 T (10,000 Gauss). Examples of electromagnets that may be used include cryo-cooled, superconducting magnetic coils capable of producing fields of several tesla.

The forces applied to the cells will generally be from 0.1 to 10 pN (as previously indicated), such forces being capable of opening transmembrane ion channels. The magnetic fields and field gradients required to generate these forces vary depending on the magnetic, volumetric and shape properties of the particles and the distance between the tissue construct and the magnet. These parameters are governed by the equation:

$$F_{mag} = (\chi_2 - \chi_1) V \frac{1}{\mu_0} B(\nabla B)$$

where $\chi_2$ is the volume magnetic susceptibility of the magnetic particle, $\chi_1$ is the volume magnetic susceptibility of the surrounding medium (i.e. tissue/bone), $\mu_o$ is the magnetic permeability of free space, B is the magnetic flux density in Tesla (T). Though this assumes spherical particles and no magnetic dipole interactions, it should give a good approximation of the field and gradient required for the system.

As the value of $\chi_1$ for human tissue is very small and negative in comparison with the magnetic susceptibility of magnetite (or other magnetic material which will be used in the ferrofluids, and nanoparticles), $\chi_1$ is negligible for this calculation and the expression $(\chi_2 - \chi_1)$ can be reduced to $\chi_2$. Also, as we are interested in the translational motion of the magnetite particle/fluid/material in an applied field along the z-axis (vertical) and, assuming a relative permeability of 1, the force expression can be reduced to:

$$F_{mag} = (\chi_2) V B \frac{dB}{dz}$$

for particles close to the magnetic field source.

It can be seen from these equations that the compressional (translational) force experienced by the tissue constructs in the presence of ferrofluids and magnetic particles is dependent on the strength of the field, the field gradient and the volumetric and magnetic properties of the particles. One of these parameters will have a strong spatial variation—the field strength/gradient product. This will enable the application of differential forces in three dimensions. In addition, by seeding different regions of the scaffold with particles, ferrofluids and magnetic materials of differing magnetic and volumetric properties, the three-dimensional variation in applied force can be enhanced. This facilitates the growth of complex tissue structures via the spatial variation of applied forces inside the bioreactor.

A number of different scaffold types (essentially 3-dimensional porous blocks which can be varied in dimension) can be used. One of the advantages of the present invention is that the scaffolds do not need enhanced mechanical properties as the stresses involved are generally small. It is possible, for example, to use a biodegradable, porous polylactic acid (PLA) based scaffold. Alternative scaffolds include PGA (poly glycolic acid) materials which are rapidly degrading and are less mechanically strong and collagen scaffolds which are natural materials [7]. The scaffold may be coated with collagen type 1 or other adhesion molecules (such as RGD or non-RGD based molecules) to improve cell adhesion.

The invention will be illustrated, by way of example only, with reference to the accompanying drawings, in which.

Figure 1:
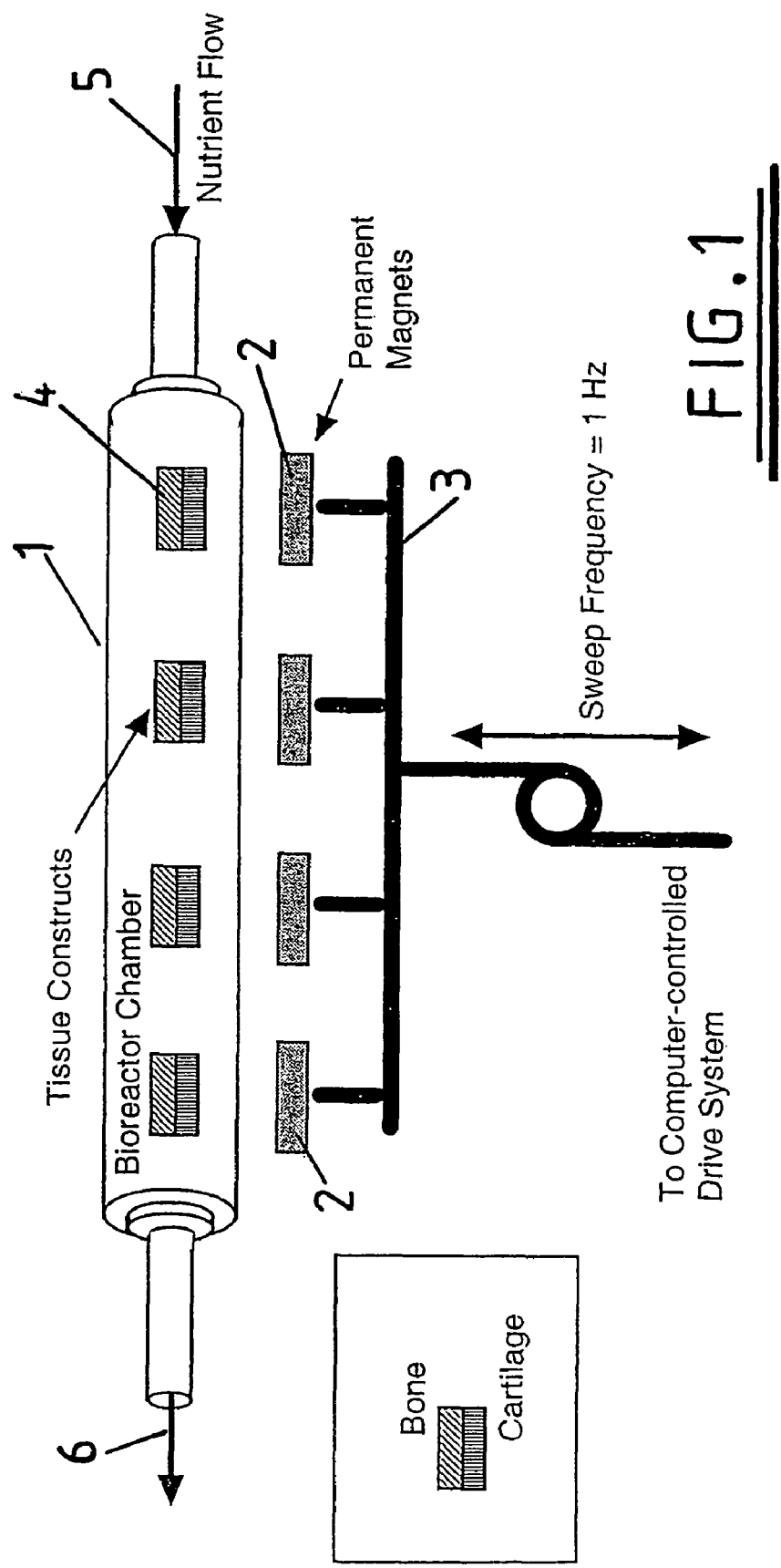
FIG. 1 illustrates a first embodiment of the invention.

Referring to FIG. 1, there is illustrated a tubular bioreactor 1 associated with permanent magnets 2 which are positioned externally of the reactor 1 and which are mounted on a carrier arrangement 3 connected to a computer-controlled (or other time-varying) drive system not illustrated in detail in the drawings.

Within the bioreactor 1 are a number of longitudinally spaced tissue constructs 4 each depicted as being comprised on bone tissue on one side (the side remote from the magnets 3) and cartilage tissue on the other side (other tissue types may also be used). The tissue cells have magnetic beads (not shown) attached thereto and are seeded on 3-D scaffolds (again not shown). Nutrients are supplied to the bioreactor as depicted by arrow 5 and exit therefrom as depicted by arrow 6.

There are a total of four magnets 2 (though this number can vary to match the number of tissue constructs) which are external of the bioreactor and longitudinally spaced therealong. The positioning of the magnets is such that there is one magnet associated with each of the tissue constructs, the magnets being provided on the cartilage sides thereof.

In use of the apparatus, the carrier is driven so as to oscillate the magnets transversely towards and away from the bioreactor. The oscillation frequency at which the magnets are driven will usually be varied and generally be in the range of 0.1 to 10 Hz although values outside this range may be used.

The oscillation of the magnets stimulates a compression/ relaxation cycle which is applied to the tissue constructs, the frequency of which can also be varied by mechanical drivers (not shown) attached to the magnets. The magnet field gradient (spatially varying magnetic field strength) ensures that the cartilage experiences slightly higher flux densities than the bone cells.

Strong magnetic field gradients will produce a translational motion on the nanoparticles directed towards the magnets, compressing the cells and scaffold inside the bioreactor. This compression will simulate mechanical loading without requiring direct access to the cells inside the bioreactor. Loads can be easily varied by changing the magnetic field strength and gradient, magnet position and/or the physical properties of the nanoparticles compressing the tissue constructs.

If desired, the magnetic particles associated with the bone cells may have different magnetic properties from those associated with the cartilage so that different mechanically stresses are applied to the two different types of cells.

Figure 2:
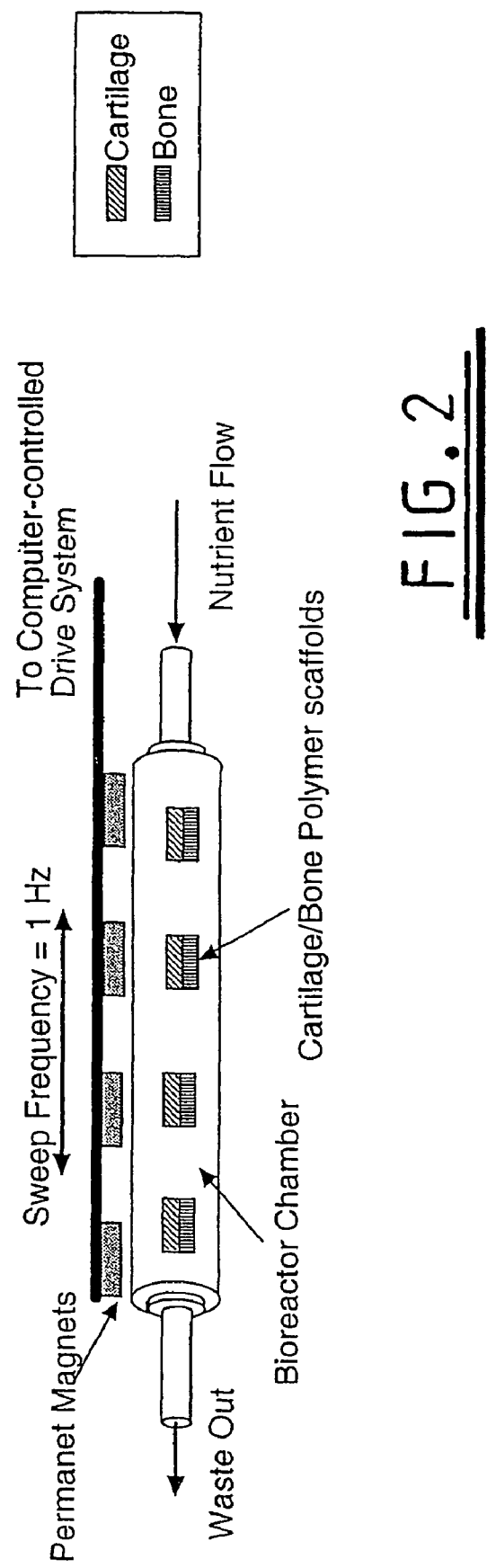
FIG. 2 illustrates a second embodiment of the invention.

FIG. 2 illustrates a modification of the apparatus shown in FIG. 1. In the modification of FIG. 2, the (permanent) magnets are oscillated parallel to the longitudinal axis of the bioreactor (rather then transversely to the axis in the case of FIG. 1).

A number of modifications may be made to the illustrated embodiments.

Thus, for example, the magnets may be swept relatively around the bioreactor. This may most conveniently, but not necessarily, be achieved by keeping the magnets fixed and rotating the bioreactor around its longitudinal axis.

Alternatively or additionally the permanent magnets illustrated in FIGS. 1 and 2 may be replaced by electromagnets. A further possibility is for the nanoparticles attached to the cells to be replaced by ferrofluids. If desired, a combination of attached nanoparticles and ferrofluids may also be used.

A further possibility is to use magnetic/metal plates or other structures which could be attracted to the magnets in order to deform the entire scaffold.

Figure 3:
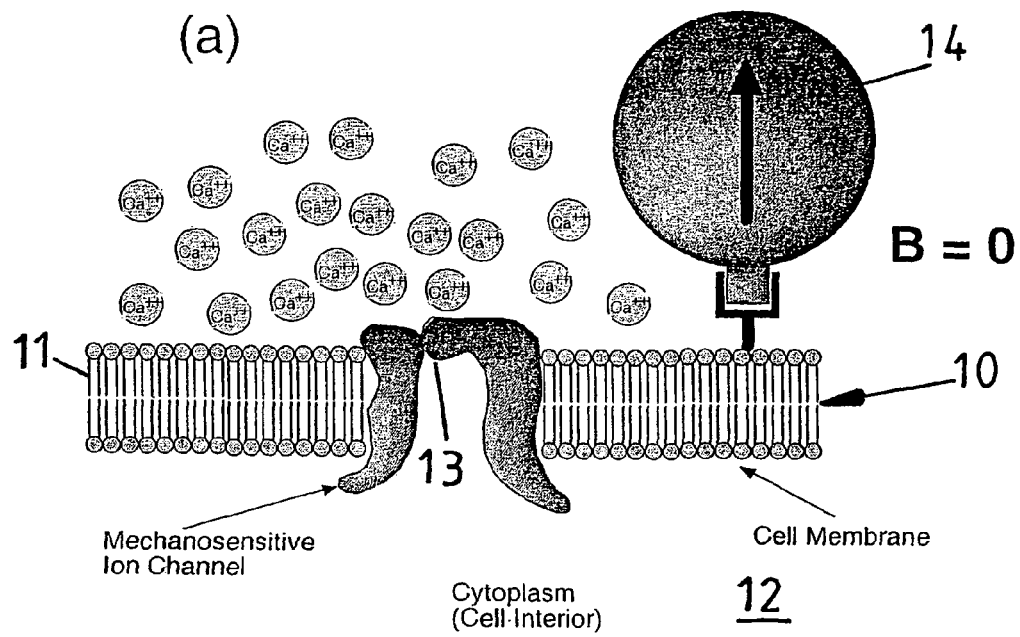
FIG. 3 illustrates activation of a mechano-sensitive transmembrane ion channel by the use of a magnetic field.
Figure 3:
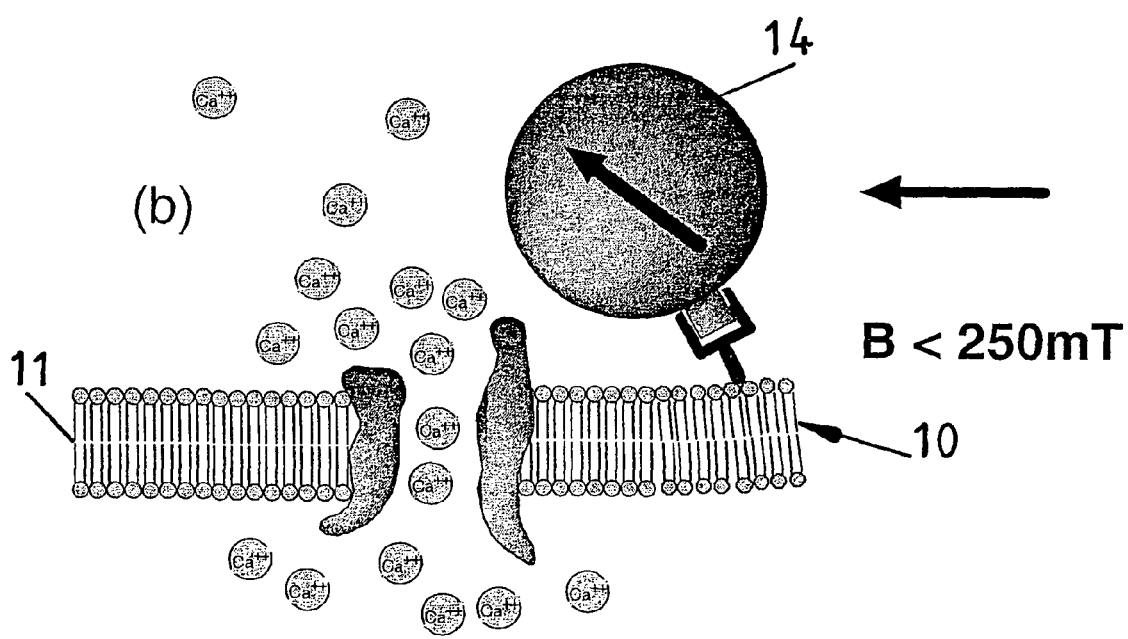

Reference is now made to FIG. 3 which illustrates an alternative method of activation of mechano-sensitive transmembrane ion channels by the use of a magnetic field so as to simulate period mechanical loading of a tissue construct.

More particularly, FIG. 3 illustrates a cell 10 having a membrane 11 enclosing the cell's cytoplasm 12. Within membrane 11 is a mechanosensitive ion channel 13. A functionalized magnetically blocked particle 14 (such as Sphereotech's coated ferromagnetic particles, d=4.5 μm) is rigidly attached to the cell membrane 11 either directly or indirectly via cytoskeletal coupling [8, 9].

In the condition shown in FIG. 3($a$), no magnetic field is applied to the cell 10 and the ion channel 13 is closed.

By oscillating a magnetic field source (not shown) the magnetic particle 14 attached to the cell 10 can be twisted, exerting a mechanical stress on the cell membrane 11 and activating the mechano-sensitive ion channel 13 (FIG. 3$b$). This ion channel activation initiates biochemical reaction pathways in the cells being [4] cultured and simulates periodic echanical loading of tissue constructs inside the bioreactor.

REFERENCES

1. Ying, Y., Peak, M., Magnay, J., and El Haj, A. J. (2000) Dynamic cell scaffold interactions: implications for tissue engineering. *Proceedings of the second Smith and Nephew international symposium on tissue engineering,* York, UK
2. El Haj, A J, L M Walker, M R Preston, S J Publicover (1999) Mechanotransduction pathways in bone: calcium fluxes and the role of voltage-operated calcium channels. *Med. Biol. Eng. Comp.,* 37: 403-409.
3. Howard J and A J Hudspeth (1989) Compliance of the hair bundle associated with the gating of mechanoelectrical transduction channels in the bullfrog's saccular hair cell. *Neuron* 1: 189-199.
4. Walker et al J Cell Biochem 2000.
5. Pardoe, H, W Chua-anusorn, T G St. Pierre, J Dobson (2000) Structural and magnetic properties of nanoscale magnetic particles synthesised by coprecipitation of iron oxide in the presence of dextran or polyvinyl alcohol. *J. Magn. Mag. Materials.* In Press.
6. Tan, W, S Santra, Z Peng, R Tapec and J Dobson (2000) Coated nanoparticles. U.S. Patent Pending (Filed May 17, 2000).
7. Sittinger et al 1996.
8. Kirschvink, J L (1992) Comments on "Constraints on biological effects of weak extremely-low-frequency electromagnetic fields". *Phys. Rev. A.* 46: 2178-2184.
9. Dobson, J and T G St. Pierre (1996) Application of the Ferromagnetic Transduction Model to D.C. and Pulsed Magnetic Fields: Effects on Epileptogenic Tissue and Implications for Cellular Phone Safety. *Biochem. Biophys. Res. Commun.,* 227:718-723.

The invention claimed is:

1. A method of mechanically stimulating cells for tissue engineering applications, comprising:
    (a) culturing tissue-forming cells in the presence of a magnetic material, the magnetic material being capable of generating a force in response to an applied magnetic field and transmitting the force to the tissue-forming cells, wherein the magnetic material comprises a ferrofluid; and (b) applying a magnetic field to the magnetic material, whereby mechanical stress is applied to the tissue-forming cells by means of linear translational motion of the magnetic material in response to the applied magnetic field.

2. The method of claim 1, wherein the tissue-forming cells are grown on or in a three-dimensional scaffold.

3. The method of claim 1, wherein the tissue-forming cells are cultured in a bioreactor through which flows a culture medium.

4. The method of claim 1, wherein the magnetic field is applied from external to the bioreactor.

5. The method of claim 1, wherein functional tissue is produced.

6. A method of mechanically stimulating cells for tissue engineering applications, comprising:
  (a) culturing tissue-forming cells in the presence of an exogenous magnetic material, the magnetic material being capable of generating a force in response to an applied magnetic field and transmitting the force to the tissue-forming cells; and
  (b) applying a magnetic field to the magnetic material, whereby mechanical stress is applied to the tissue-forming cells by means of linear translational motion of the magnetic material in response to the applied magnetic field, and wherein the method is applied in vivo to grow tissue in situ within a patient's body.

7. A method of mechanically stimulating cells for tissue engineering applications, comprising:
  (a) culturing tissue-forming cells in the presence of an exogenous magnetic material, the magnetic material being capable of generating a force in response to an applied magnetic field and transmitting the force to the tissue-forming cells, wherein the magnetic material is attached to the tissue-forming cells; and
  (b) applying a magnetic field to the magnetic material, whereby mechanical stress is applied to the tissue-forming cells by means of linear translational motion of the magnetic material in response to the applied magnetic field.

8. The method of claim 7, wherein the magnetic material comprises micro- or nano-particles.

9. The method of claim 7, wherein the magnetic field is varied during culture of said tissue-forming cells.

10. The method of claim 9, wherein the magnetic field is varied sinusoidally.

11. The method of claim 10, wherein the magnetic field is varied at a frequency of 0.1 to 10 Hz.

12. The method of claim 7, which is applied in vitro.

13. The method of claim 12, wherein the tissue-forming cells are grown on or in a three-dimensional scaffold.

14. The method of claim 13, wherein the tissue-forming cells are cultured in a bioreactor through which flows a culture medium.

15. The method of claim 14, wherein the magnetic field is applied from external to the bioreactor.

16. The method of claim 7, wherein the cells being cultured are for forming connective tissue.

17. The method of claim 16, wherein the cells being cultured are for forming bone, cartilage, ligament or tendons.

18. The method of claim 7, wherein at least a first cell type and a second, different, cell type are cultured.

19. The method of claim 18, wherein the mechanical stress applied to the first cell type differs from the stress applied to the second cell type in at least one property selected from the group consisting of: magnitude and direction of application.

20. The method of claim 18, wherein the cells being cultured comprise bone-forming cells and cartilage-forming cells.

21. The method of claim 7, wherein the forces applied to the cells or a scaffold are in the range 0.01 to 100 picoNewtons.

22. The method of claim 7, wherein functional tissue is produced.

* * * * *